(12) United States Patent
Suresh et al.

(10) Patent No.: US 6,319,244 B2
(45) Date of Patent: *Nov. 20, 2001

(54) CATHETER WITH FLEXIBLE AND RIGID REINFORCEMENTS

(75) Inventors: Mitta Suresh; Albert Davis, both of Richardson, TX (US)

(73) Assignee: Chase Medical, L.P., Richardson, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/268,980

(22) Filed: Mar. 16, 1999

(51) Int. Cl.[7] .................................................. A61M 25/00
(52) U.S. Cl. ......................... 604/525; 604/526; 604/530
(58) Field of Search ................................... 604/523–526, 604/528, 530, 532, 915, 912, 96.01

(56) References Cited

U.S. PATENT DOCUMENTS

| | | |
|---|---|---|
| 2,936,761 | 5/1960 | Snyder . |
| 3,802,418 | 4/1974 | Clayton . |
| 3,884,242 | 5/1975 | Bazell et al. . |
| 3,902,492 | 9/1975 | Greenhalgh . |
| 3,913,565 | 10/1975 | Kawahara . |
| 3,983,879 | 10/1976 | Todd . |
| 4,055,187 | 10/1977 | Patel et al. . |
| 4,251,305 | 2/1981 | Becker et al. . |
| 4,402,684 | 9/1983 | Jessup . |
| 4,596,548 | 6/1986 | DeVries et al. . |
| 4,639,252 | 1/1987 | Kelly et al. . |
| 4,661,095 | 4/1987 | Taller et al. . |
| 4,702,252 | 10/1987 | Brooks et al. . |
| 4,899,787 * | 2/1990 | Ouchi et al. ......................... 138/131 |
| 4,913,683 * | 4/1990 | Gregory ................................. 604/8 |
| 5,041,084 | 8/1991 | DeVries et al. . |
| 5,069,674 | 12/1991 | Fearnot et al. . |
| 5,176,661 * | 1/1993 | Evard et al. . |

(List continued on next page.)

FOREIGN PATENT DOCUMENTS

| | | |
|---|---|---|
| 867 144 | 4/1951 | (DE) . |
| 0 451 996 A1 | 10/1991 | (EP) . |
| WO 97/32623 | 9/1997 | (WO) . |
| WO 98/48884 | 11/1998 | (WO) . |
| WO 99/04848 | 2/1999 | (WO) . |

*Primary Examiner*—Anhtuan T. Nguyen
*Assistant Examiner*—Jeremy Thissell
(74) *Attorney, Agent, or Firm*—Haynes & Boone, LLP

(57) ABSTRACT

A catheter (10, 38, 40, 50, 80, 90) having both a flexible (30) and a rigid reinforcement section (36). The catheter body (12) is comprised of an elastomeric material, such as silicone, having a resilient coil or spring member (30) within a fluid delivery lumen (20) along the proximal portion (14) thereof. The catheter is provided with a more rigid malleable reinforcement member (36) at the distal portion (16) thereof, also extending within the fluid delivery lumen (20) and positioned proximal the coil member (30) within the fluid delivery lumen (20). The rigid reinforced distal portion (16) of the catheter body helps the surgeon to hold the tip of the catheter more firmly, and makes insertion of the catheter tip into the body vessel easier. The more flexible support portion (30) at the proximal portion (14) of the elastomeric catheter body reinforces the catheter to prevent kinking, yet allows flexibility to facilitate the surgeon to move the proximal portion (14) of the catheter out of the surgical site. The catheter body may be provided with a balloon (56) and a hinge portion (42), such as defined by an annular detent (54), to allow the catheter tip to self-align within the body vessel when the balloon is inflated. Both the flexible (30) and rigid (36) reinforcement sections are tubular to facilitate fluid delivery therethrough within through the lumen (20) through which the reinforcement members (30 and 36) reside.

29 Claims, 3 Drawing Sheets

U.S. PATENT DOCUMENTS

| | | |
|---|---|---|
| 5,195,969 | 3/1993 | Wang et al. . |
| 5,217,466 * | 6/1993 | Hasson .................................. 606/119 |
| 5,254,091 | 10/1993 | Aliahmad et al. . |
| 5,269,752 | 12/1993 | Bennett . |
| 5,279,562 | 1/1994 | Sirhan et al. . |
| 5,279,596 | 1/1994 | Castaneda et al. . |
| 5,304,131 * | 4/1994 | Paskar .................................... 604/95 |
| 5,306,245 * | 4/1994 | Heaven . |
| 5,314,418 | 5/1994 | Takano et al. . |
| 5,330,451 | 7/1994 | Gabbay . |
| 5,334,146 | 8/1994 | Ozasa . |
| 5,334,169 | 8/1994 | Brown et al. . |
| 5,344,399 | 9/1994 | DeVries . |
| 5,353,486 | 10/1994 | Saab . |
| 5,356,388 | 10/1994 | Sepetka et al. . |
| 5,358,493 | 10/1994 | Schweich, Jr. et al. . |
| 5,364,357 | 11/1994 | Aase . |
| 5,401,244 | 3/1995 | Boykin et al. . |
| 5,405,338 | 4/1995 | Kranys . |
| 5,425,708 | 6/1995 | Nasu . |
| 5,437,288 * | 8/1995 | Schwartz et al. ..................... 128/772 |
| 5,441,484 | 8/1995 | Atkinson et al. . |
| 5,441,499 * | 8/1995 | Fritzsch . |
| 5,443,448 | 8/1995 | DeVries . |
| 5,448,989 * | 9/1995 | Heckele ................................ 600/142 |
| 5,449,343 | 9/1995 | Samson et al. . |
| 5,460,608 * | 10/1995 | Lodin et al. ............................ 604/96 |
| 5,462,523 | 10/1995 | Samson et al. . |
| 5,470,313 | 11/1995 | Crocker et al. . |
| 5,477,856 * | 12/1995 | Lundquist . |
| 5,484,409 | 1/1996 | Atkinson et al. . |
| 5,569,219 | 10/1996 | Hakki et al. . |
| 5,593,394 | 1/1997 | Kanesaka et al. . |
| 5,599,325 | 2/1997 | Ju et al. . |
| 5,605,162 | 2/1997 | Mirzaee et al. . |
| 5,607,394 | 3/1997 | Anderson et al. . |
| 5,624,380 * | 4/1997 | Takayama et al. . |
| 5,634,895 | 6/1997 | Igo et al. . |
| 5,645,560 | 7/1997 | Crocker et al. . |
| 5,653,696 | 8/1997 | Shiber . |
| 5,658,251 | 8/1997 | Ressemann et al. . |
| 5,658,264 * | 8/1997 | Samson ................................ 604/282 |
| 5,662,607 | 9/1997 | Booth et al. . |
| 5,695,483 | 12/1997 | Samson . |
| 5,700,253 * | 12/1997 | Parker .................................. 604/282 |
| 5,755,687 | 5/1998 | Donlon . |
| 5,769,828 | 6/1998 | Jonkman . |
| 5,795,332 | 8/1998 | Lucas et al. . |
| 5,795,341 | 8/1998 | Samson . |
| 5,836,926 * | 11/1998 | Peterson et al. ..................... 604/264 |
| 5,843,116 | 12/1998 | Crocker et al. . |
| 5,865,721 * | 2/1999 | Andrews et al. ....................... 600/18 |
| 5,873,866 * | 2/1999 | Kondo et al. ........................ 600/140 |
| 5,911,734 * | 6/1999 | Tsugita et al. ....................... 606/200 |
| 5,941,858 * | 8/1999 | Johnson ............................... 600/423 |
| 5,947,940 | 9/1999 | Beisel . |
| 5,951,539 * | 9/1999 | Nita et al. ............................ 604/526 |
| 6,135,982 * | 10/2000 | Campbell . |

* cited by examiner

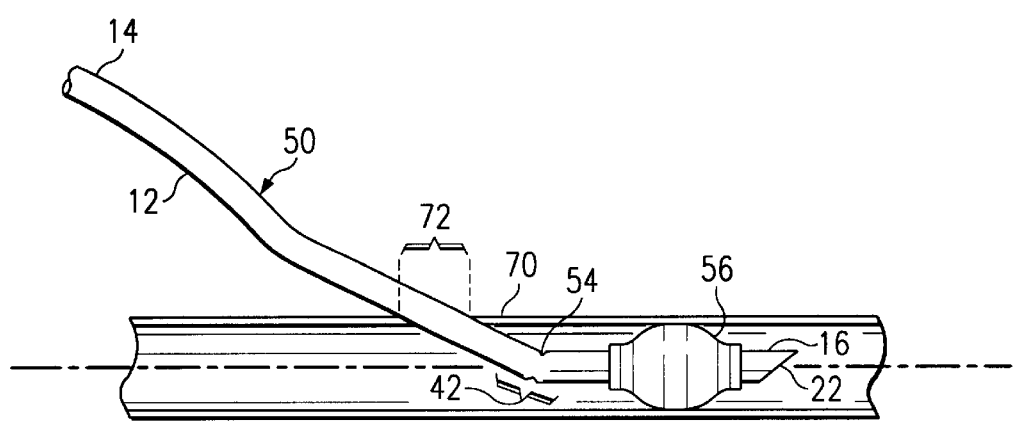
FIG. 5
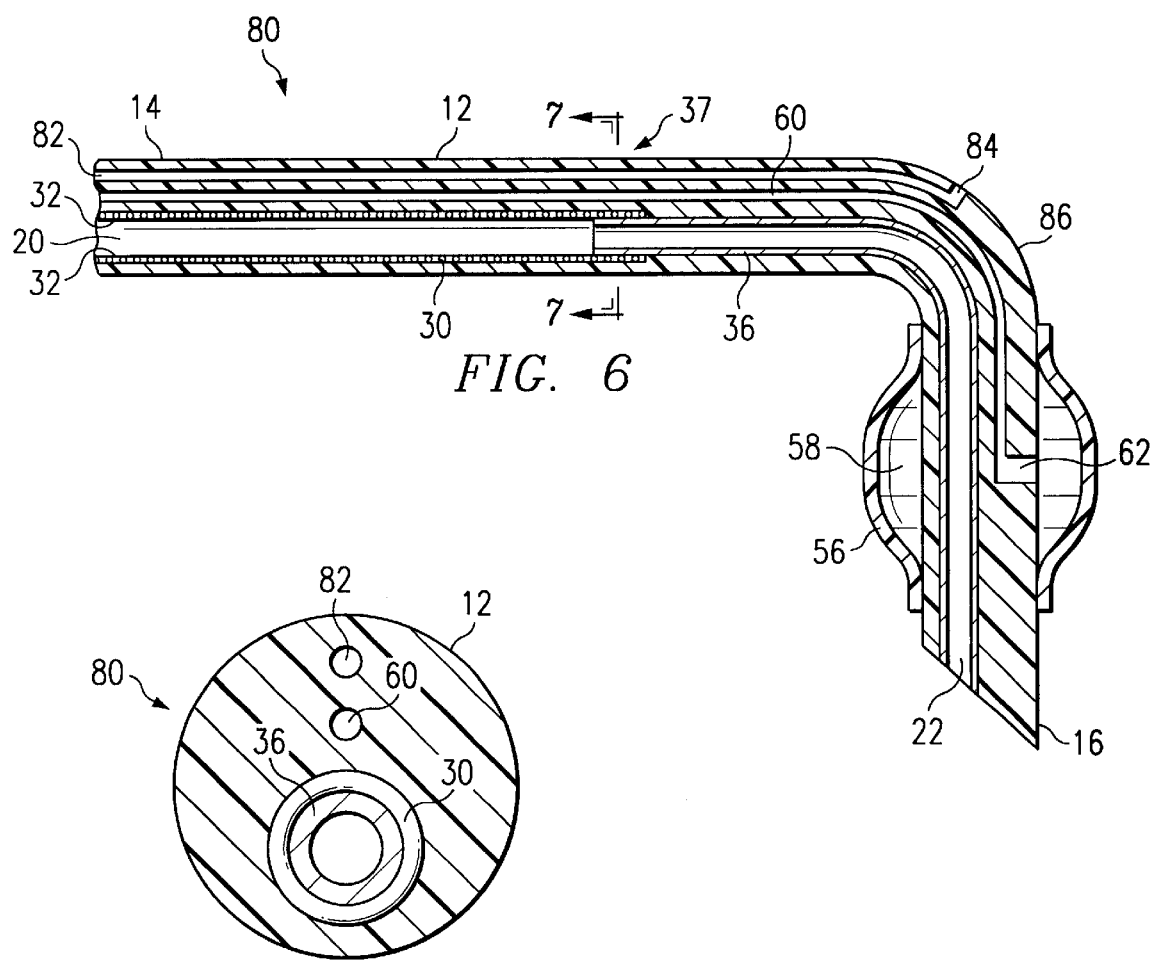
FIG. 6
FIG. 7

CATHETER WITH FLEXIBLE AND RIGID REINFORCEMENTS

CROSS REFERENCE TO RELATED APPLICATIONS

The following U.S. patent application is commonly assigned and is incorporated herein by reference:

| Patent No. | Serial No. | Title | Filed |
|---|---|---|---|
| TBD | TBD | Catheter Having Varying Resiliency Balloon | Herewith |

FIELD OF THE INVENTION

The present invention is generally related to medical catheters, and more particularly to catheters subject to high insertion and manipulation forces such as aortic perfusion catheters and the like.

BACKGROUND OF THE INVENTION

One of the challenges surgeons face during surgery while connecting catheters to body vessels, such as arteries, is the difficulty of inserting and manipulating the catheters within the body vessels. It is preferred to have the catheter body comprised of a softer material so that the catheter body does not create trauma to the body vessels. However, softer catheter bodies are more difficult to insert and manipulate within the body vessels, because they have reduced body strength. One way to stiffen the softer catheter body is to place the catheter in an ice slush before inserting it into the body vessel. By lowering the temperature of the catheter body, the surgeon is able to temporarily stiffen the catheter body, which is typically made of a material such as polyvinylchloride (PVC), polyurethane, polyethylene and the like.

The problems presented by soft catheter bodies during insertion and manipulation are more apparent when the catheter bodies are made of elastomeric materials. Elastomeric materials, such as silicone, are quite desirable for inflatable balloons and catheter bodies since they are atraumatic, but suffer in that these materials cannot be bonded to other conventional non-similar materials such as PVC, polyurethane and polyethylene.

Silicone catheter bodies usually need to be structurally reinforced to provide body strength and kink resistance to avoid collapsing during use. One conventional form of reinforcement is to provide a coil integrally formed in the catheter body outerwall. This coil reinforcement gives flexibility to the catheter while at the same time providing kink resistance. Flexibility of the catheter at all times is desired because the surgeon would like to clear the catheter body out from a surgical site once he secures the catheter in the body vessel. However, a coil may not provide sufficient body strength for inserting and manipulating the catheter within a body vessel.

There is desired an improved catheter preferably comprised of an atraumatic elastomeric material, such as silicone, which has improved resistance from collapsing and kinking, and also has sufficient body strength to facilitate insertion and maneuvering within a body vessel, such as the aorta.

SUMMARY OF THE INVENTION

The present invention achieves technical advantages as a catheter comprised of an elastomeric material and reinforced with two different reinforcement elements. The distal tip portion of the catheter is reinforced with a rigid tubular member, while the proximal portion of the catheter is reinforced with a more flexible member such as a coil or spring. The rigid tubular member is preferably malleable to allow custom shaping, and to provide body strength during insertion and manipulation. The spring and rigid tubular member preferably extend within a common lumen.

In one embodiment, the diameter of the coil or spring is about the same as the outer diameter of the tubular member, and the coil or spring is securely disposed about the rigid tubular member within a common lumen of the catheter body. In another embodiment, the outer diameter of the spring is about the same as the inner diameter of the rigid tubular member, and the spring securely resides within the tubular member. In yet another embodiment, the support members are slightly spaced from one another. In all embodiments, the coil or spring extends within one of the lumens of the catheter body, whereby a thin layer of polymeric material coats the lumen wall to encapsulate the coil or spring reinforcing member and provide a smooth surface in the flow lumen.

An elastomeric balloon may be sealingly attached about the catheter body and may be comprised of a material compatible with the catheter body, both preferably being comprised of silicone. A hinge is preferably provided in the catheter body proximal to the rigid tubular member to allow hinging the catheter body distal portion within a body vessel after insertion. The hinge allows the balloon and catheter distal portion to self-align within the center of the body vessel.

Also disclosed is a method of manipulating a catheter within a body vessel including the steps of inserting the catheter into the vessel and advancing the catheter in the vessel such that the catheter distal portion is positioned along the length of the vessel. The catheter has a lumen extending between a proximal portion and a distal portion, and has a resilient support member extending about the lumen from the catheter proximal portion to a location short of the distal portion. The catheter also has a tubular rigid support member extending about the lumen from proximate the resilient member distal portion to the catheter distal portion. Optional steps include holding the rigid support member of the catheter during advancement, infusing a fluid into the body vessel, aspirating a fluid from the body vessel, and inflating an optional elastomeric balloon to occlude a portion of the body vessel. Preferably, the distal portion of the catheter remains positioned parallel to the length of the vessel during the steps of advancing and manipulating the catheter to avoid damage to the inner walls of the body vessel.

The rigid reinforced section at the distal tip of the catheter body allows the surgeon to hold the catheter tip more firmly during insertion and manipulation within a body vessel. Because the tip is rigid, the catheter tip is more controllable within the body vessel, such as the aorta. Because the catheter section proximal the rigid tip is reinforced by the spring or coil member, this portion of the catheter is flexible and resists kinking. This more flexible section, however, allows the surgeon to move the catheter proximal portion out of the surgical site without kinking.

BRIEF DESCRIPTION OF THE DRAWINGS

FIG. 5 is an illustration of the catheter of FIG. 4 in use depicting the hinging and self-alignment of the balloon in the body vessel;

FIG. 6 is a cross-sectional view of a fifth embodiment of the invention including a third lumen and aspiration ports;

FIG. 7 is a cross-section taken along line 7—7 in FIG. 6 illustrating the reinforcing coil and rigid support member extending within a common lumen of an elastomeric catheter body.

DESCRIPTION OF THE PREFERRED EMBODIMENTS

Figure 1:
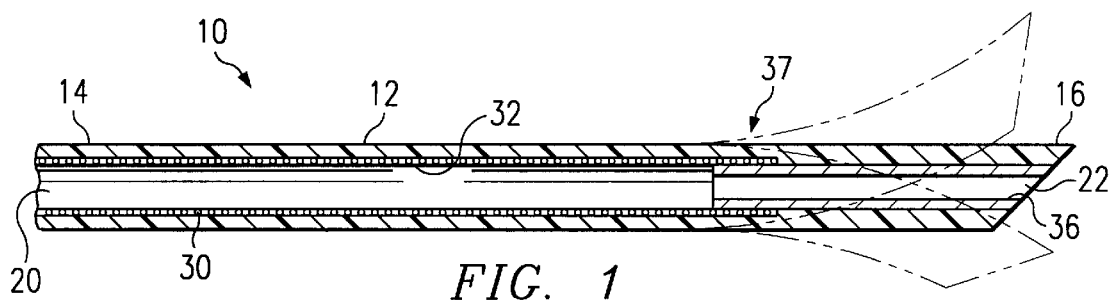
FIG. 1 is a cross-sectional view of the catheter according to a first preferred embodiment of the present invention having two different reinforcement elements connected to one another and extending within a common flow lumen of the catheter body.

Referring to FIG. 1, there is generally shown at 10 an improved catheter according to a first preferred embodiment of the present invention. Catheter 10 is seen to be comprised of an elastomeric catheter body 12 extending from a proximal end portion 14 to a tapered distal end portion 16. Extending within catheter body 12 is seen to be a first fluid delivery lumen 20 extending from the proximal portion 14 to the distal portion 16 and terminating at a lumen distal port 22. Catheter body 12 is preferably comprised of an elastomeric material such as silicone, which is a rather soft material having the advantage that it does not readily create trauma to body vessels when inserted therewithin.

Catheter body 12 is seen to be reinforced along a proximal section by a flexible coiled support member 30 comprising a coil or spring. Flexible support member 30 has a relatively small diameter and longitudinally extends within the fluid delivery lumen 20. Flexible support member 30 is sealed within the catheter body 12 with a thin layer polymeric material 32 to encapsulate the flexible support member 30 and provide a smooth flow lumen wall. According to the present invention, the distal portion of the catheter body is provided with a malleable tubular rigid support member 36 reinforcing the distal portion 16 of catheter body 12. The rigid support member 36 allows the catheter distal end to be bent and customly shaped, as shown by the phantom lines. The rigid support member 36 also structurally reinforces the catheter distal portion 16 such that it can be securely grasped by the surgeon during insertion and manipulation within a body vessel. The rigid support member 36 extends within the same fluid delivery lumen 20 as flexible support member 30, and is securely connected thereto at the distal end of the flexible support member 30 as shown.

Figure 8:
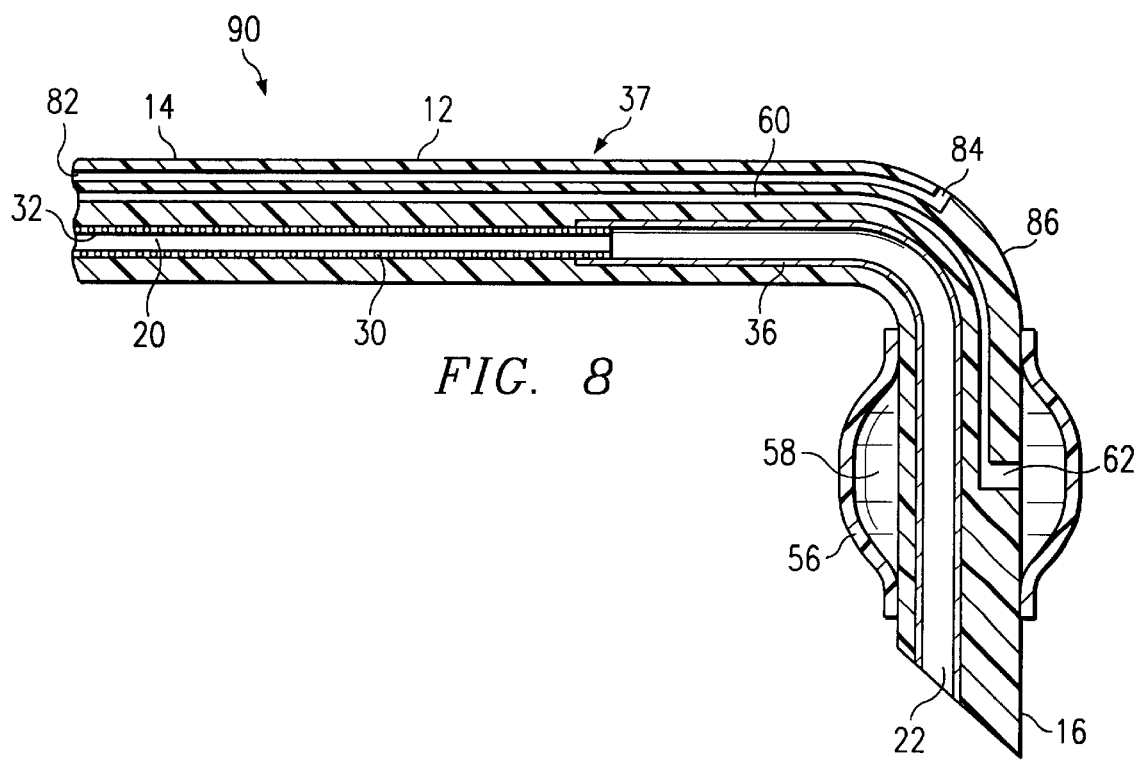
FIG. 8 is a n other embodiment of the invention with the coil member connected within the more rigid tubular support member.

As shown in the embodiment of FIG. 1, the flexible support member 30 has an inner diameter that is about the same dimension as the outer diameter of the rigid tubular support member 36 such that the spring is securingly disposed over and about the rigid tubular support member 36, shown in region 37. However, in an alternative embodiment of the invention, such as shown in FIG. 8 which will be discussed shortly, the outer diameter of the flexible support member 30 may be about the same dimension as the inner diameter of the rigid tubular support member 36 such that the flexible support member 30 is securingly positioned within the inside of the tubular support member 36.

Figure 2:
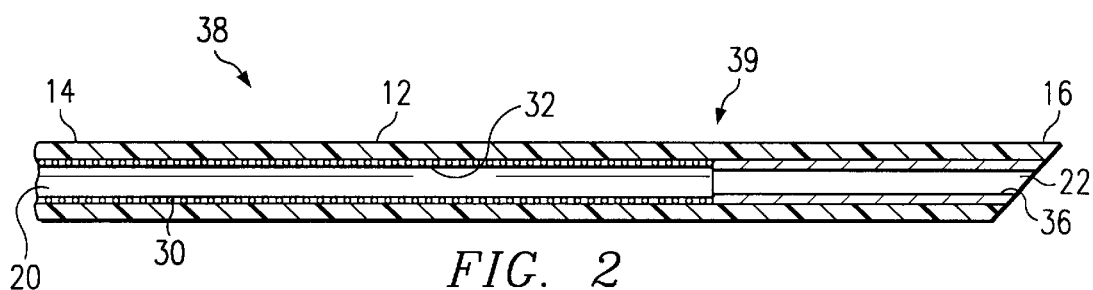
FIG. 2 is a cross-sectional view of a second embodiment of the invention wherein the two reinforcement elements abut one another.

Referring now to FIG. 2, there is shown a second embodiment of the invention identified as catheter 38. The flexible support member 30 abuts the proximal portion of the rigid support member 36, and may be securingly attached thereto if desired. According to this embodiment of the present invention, the flexible support member 30 is adjacent to the rigid support member 36 to provide a flush transition within the common flow lumen 22, shown in region 39.

Figure 3:
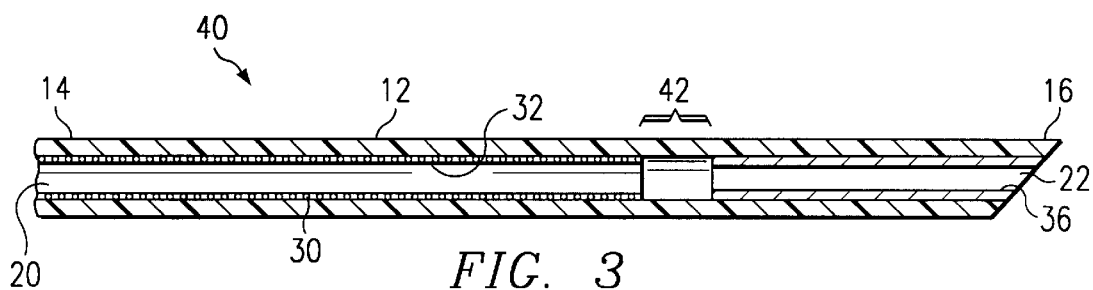
FIG. 3 is a cross-sectional view of a third embodiment of the invention wherein the two reinforcement elements are spaced from one another.

Referring now to FIG. 3, there is shown a third embodiment of the present invention shown as catheter 40. Catheter 40 is similar to catheter 10 of FIG. 1 and catheter 38 of FIG. 2, wherein like numerals refer to like elements. In this embodiment, the distal end of the flexible support member 30 is closely proximate, but spaced apart from, the proximal end of the rigid tubular support member 36 to define a flexible catheter portion shown as a thinned catheter wall at 42. Flexible portion 42 forms a hinge in the catheter body 12, and is located proximal the rigid tubular support member 36. Hinge 42 allows the distal end 16 of catheter 40 to be hinged with respect to the catheter portion reinforced and supported by the flexible support member 30 as illustrated in FIG. 5, which will be discussed shortly.

Figure 4:
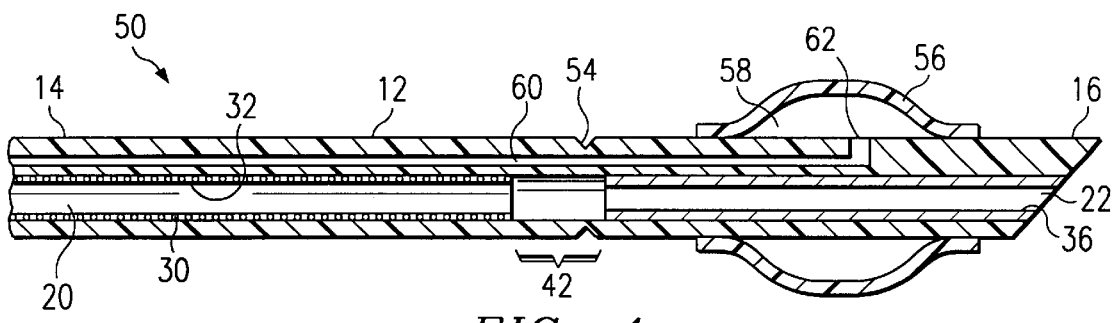
FIG. 4 is a cross-sectional view of a fourth embodiment of the invention including a balloon and a second lumen.

Referring now to FIG. 4, there is shown generally at 50 a fourth embodiment of the present invention which is similar to the catheter 10 of FIG. 1, catheter 38 of FIG. 2 and catheter 40 of FIG. 3, wherein like numerals refer to like elements. As shown in FIG. 4, the hinge portion 42 further includes an annular detent 54 which is defined by an annular recess circumferentially defined about the catheter body 12 proximal of the rigid tubular support member 36. This annular detent 54 further defines the catheter hinge such that the catheter distal end 16 can be hinged with respect to the proximal end of the catheter, as illustrated in FIG. 4. A. balloon member 56 is sealingly disposed about the distal end 16 of catheter body 12 and forms a balloon cavity 58 therebetween. The balloon member 56 is inflatable and preferably comprises silicone. A balloon inflation lumen 60 is seen to extend from proximal end 14 to distal end 16 of catheter body 12, which lumen terminates at a balloon inflation port 62 opening into balloon cavity 58. The balloon member 56 may be inflated to selectively occlude a portion of a body vessel such as an aorta during surgery, for example.

In the embodiment shown in FIG. 4, the distal end of the coiled flexible support member 30 is seen to be spaced from the proximal end of the rigid tubular support member 36. However, the distal end of flexible support member 30 could abut the proximal end of rigid support member 36 as shown in FIG. 2, or be securingly connected to the rigid support member 36 such as discussed with reference to catheter 10 in FIG. 1. Annular detent 54 can be provided in all embodiments to provide a hinge to facilitate hinging the distal end 16 at a predefined point of the catheter body, as shown in FIG. 5.

Referring to FIG. 5, the hinge 42 including detent 54 provides technical advantages by allowing the distal end 16, including the balloon 56, to self-align itself within a body vessel after insertion, as shown. The catheter 50 can be inserted through an opening 72 formed in the body vessel wall 70 at an angle, wherein the hinge 42, which may include the annular recess 54 defining a thinned body wall, allows the distal end 16 to coaxially self-align a central axis along the length of the body vessel 70, as shown. Thus, the lumen output port 22 is coaxially aligned within the center of the body vessel 70 and remains substantially parallel to the length of the body vessel 70 during advancement. During insertion and manipulation of the catheter into the body vessel, the distal end 16 supported by the rigid support member 36 can be firmly gripped by the surgeon. Again, the rigid support member 36 prevents the distal end 16 of the catheter 50 from kinking, and is malleable such that it can be customly curved and formed as desired.

Referring now to FIG. 6, there is shown a fifth embodiment of the present invention shown as catheter 80. Catheter 80 is similar to the catheters of FIG. 1, FIG. 2, FIG. 3 and FIG. 4 wherein like numeral refer to like elements. Catheter 80 further includes an aspiration/venting lumen 82 extending within catheter body 12 from the proximal end 14 toward the distal end 16 of the catheter body 12, and terminates at an aspiration port 84. The flexible coiled support member 30 is seen in this embodiment to be securingly attached to and disposed about the proximal end of the rigid support member 36 in region 37, similar to catheter 10 in FIG. 1. Again, the flexible support member 30 could also abut or be spaced from the proximal end of the rigid support member 36 as discussed with reference to the previous embodiments. As shown in FIG. 6, the malleable rigid support member 36 allows the distal end of the catheter to be custom-shaped and curved as desired by the physician, depending on the intended use. For instance, as shown in FIG. 6, the distal portion of the catheter 80 is seen to be curved at approximately 90 degrees. The catheter 80 shown in FIG. 6, for instance, is suitable for insertion into the aorta and other body vessels. The balloon 56 can be defined between a formed curved section 86 and the catheter distal end 16 to facilitate use within the aorta. The present invention finds one ideal use to provide aortic perfusion, whereby the distal tip 16 of the catheter is inserted into the aorta to perfuse the aorta with oxygenated blood. However, the catheters of the present invention are ideally suited for other surgical procedures as well, including aspiration, for example, draining blood from the vena cava. Limitation to the intended use of the embodiments of the present invention is not to be inferred.

Referring to FIG. 7, there is shown a cross-sectional view taken along lines 7—7 in FIG. 6, illustrating the flexible support member 30 being securely disposed about the proximal end of the rigid support member 36. As illustrated, the flexible coiled support member 30 and the rigid tubular support member 36 are both coaxial and positioned within the common fluid delivery lumen 20.

Referring now to FIG. 8, there is shown at 90 a catheter according to another embodiment of the present invention, which is similar to the catheter 80 of FIG. 6, wherein like numerals refer to like elements. In this embodiment, the distal end of the flexible coiled support member 30 is seen to be securely disposed within the proximal end of the rigid tubular support member 36 in region 37. However, as previously mentioned, the flexible support member 30 could also be positioned to abut the proximal end of the rigid tubular support member 36, and also could spaced therefrom if desired, such as shown in FIG. 3 and FIG. 4. Moreover, the catheter 90 could also be provided with a hinge 42, which may include a detent 54, such as shown in FIG. 4, if desired. Other ways of forming a hinge 42 are intended to be covered by the present invention and a thinned catheter wall defined by annular detent 54 depicts the preferred embodiment of the present invention.

The present invention derives technical advantages as a catheter having an elastomeric catheter body reinforced with two different reinforcement elements, a flexible reinforcement member at the proximal end and a more rigid tubular member at the distal end thereof. The rigid reinforced portion at the catheter distal tip namely, that portion reinforced by the rigid tubular member 36, allows the surgeon to hold the tip of the catheter firmly. Since this tip is rigid, the insertion and manipulation of the catheter tip 16 in a body vessel is more controllable. The proximal end 14 of the catheter 10 supported by flexible support member 30, however, is flexible yet resists kinking. This proximal portion of the catheter supported by flexible support member 30 is sufficiently flexible to facilitate the surgeon to selectively move the proximal end away from the surgical site without kinking. Thus, the present invention maintains flexibility at the proximal end with kink resistance, while provides a rigid distal tip for manipulation in the body vessel during surgery.

Both the flexible support member 30 and the rigid support member 36 are preferably comprised of stainless steel, although limitation to these materials is not to be inferred. It can be seen that the tapered distal end of the rigid tubular support member 36 lies substantially in the same plane as the tapered catheter body distal end, and thus provides a smooth distal end and ease of manipulation with the vessel member.

Though the invention has been described with respect to a specific preferred embodiment, many variations and modifications will become apparent to those skilled in the art upon reading the present application. It is therefore the intention that the appended claims be interpreted as broadly as possible in view of the prior art to include all such variations and modifications.

We claim:

1. A catheter, comprising:
a catheter body having a first lumen extending between a proximal portion and a distal portion;
a resilient support member extending about said first lumen from said catheter proximal portion to a location short of said distal portion; and
a tubular rigid support member extending about said first lumen from proximate said resilient member distal portion to said lumen distal portion; and wherein said catheter body further comprises hinge means disposed proximate said tubular rigid support member and said resilient support member for hinging said catheter body distal portion about said hinge means.

2. The catheter as specified in claim 1 wherein said hinge means comprises a detent.

3. The catheter as specified in claim 1 further comprising an inflatable elastomeric balloon disposed about said catheter distal portion and means to inflate said balloon.

4. The catheter as specified in claim 3 wherein said balloon comprises silicone.

5. The catheter as specified in claim 1 wherein said tubular rigid support member is malleable.

6. The catheter as specified in claim 5 wherein said tubular rigid support member and said catheter body distal portion is curved along a curved portion.

7. The catheter as specified in claim 6 further comprising an inflatable balloon disposed between said curved portion and said catheter distal portion, and means for inflating said balloon.

8. The catheter as specified in claim 1 further comprising a thin film disposed about said resilient support member sealing said resilient support member within said first lumen.

9. The catheter as specified in claim 1 wherein said resilient support member is secured to said tubular rigid support member.

10. The catheter as specified in claim 1 wherein said resilient support member comprises a coil.

11. The catheter as specified in claim 10 wherein said coil is disposed about and secured to said tubular rigid support member.

12. The catheter as specified in claim 10 wherein said coil is disposed within and secured to said tubular rigid support member.

13. The catheter as specified in claim 10 wherein said catheter body comprises an elastomeric material.

14. The catheter as specified in claim 13 wherein said elastomeric material comprises silicone.

15. The catheter as specified in claim 1 further comprising a second lumen extending within said catheter body to said catheter body distal portion.

16. The catheter as specified in claim 15 wherein said catheter body comprises silicone.

17. The catheter as specified in claim 1 wherein said tubular rigid support member is disposed proximate, but spaced from, said resilient support member to define a first catheter section comprising said hinge means.

18. The catheter as specified in claim 17 wherein said first catheter section further comprises a detent.

19. The catheter as specified in claim 17 wherein said first catheter section has a thinned wall thickness.

20. A catheter, comprising:
a catheter body having a first lumen extending between a proximal portion and a distal portion;
a resilient support member extending about said first lumen from said catheter proximal portion to a location short of said distal portion; and
a tubular rigid support member extending about said first lumen from proximate said resilient member distal portion to said lumen distal portion, wherein said resilient support member is disposed about and secured to said tubular support member.

21. A catheter, comprising:
a catheter body having a proximal portion, a distal portion, and a first lumen extending between a proximal end and a distal end;
a resilient support member extending about said first lumen from said proximal end to a first location between said proximal and said distal end;
a tubular rigid support member extending about said first lumen from a second location proximate to said first location to said distal end,
a hinge means for hinging said distal portion about said hinge means, wherein said hinge means is disposed between said tubular rigid support member and said resilient support member.

22. The catheter as specified in claim 21 wherein said hinge means comprises a detent.

23. The catheter as specified in claim 21 further comprising an inflatable elastomeric balloon disposed about said catheter body.

24. The catheter as specified in claim 21 wherein said tubular rigid support member and said distal portion is curved along a curved portion.

25. The catheter as specified in claim 24 further comprising an inflatable balloon disposed between said curved portion and said distal end.

26. The catheter as specified in claim 21 further comprising a thin film disposed about said resilient support member sealing said resilient support member within said first lumen.

27. The catheter as specified in claim 21 wherein said resilient support member is a coil disposed within and secured to said catheter body.

28. The catheter as specified in claim 21 wherein said tubular rigid support member is disposed proximate, but spaced from, said resilient support member to define a first catheter section comprising said hinge means.

29. The catheter as specified in claim 28 wherein said first catheter section further comprises a detent.

* * * * *